United States Patent [19]

Henley

[11] 4,214,576
[45] Jul. 29, 1980

[54] APPARATUS FOR BODY MASSAGE USING A FLUIDIZED BED APPARATUS

[76] Inventor: Ernest J. Henley, 359 Westminster, Houston, Tex. 77024

[21] Appl. No.: 840,754

[22] Filed: Oct. 11, 1977

[51] Int. Cl.² ............................................. A61H 29/00
[52] U.S. Cl. ..................................... 128/24.1; 128/38
[58] Field of Search ............. 128/24.1, 65, 66, 38–40, 128/54, 55, 62, 24 R, 25 B

[56] References Cited

U.S. PATENT DOCUMENTS

| | | | |
|---|---|---|---|
| 2,956,565 | 10/1960 | Anderson | 128/369 |
| 2,975,786 | 3/1961 | Williams | 128/65 |
| 2,998,817 | 9/1961 | Armstrong | 128/33 |
| 3,760,800 | 9/1973 | Staffin et al. | 128/24.1 |

Primary Examiner—Lawrence W. Trapp
Attorney, Agent, or Firm—Leonard S. Knox; William F. Frank

[57] ABSTRACT

An apparatus and method for therapeutic massage and heat therapy of the body or parts thereof by immersion in a fluidized solids bed.

16 Claims, 7 Drawing Figures

U.S. Patent    Jul. 29, 1980    Sheet 1 of 2    4,214,576
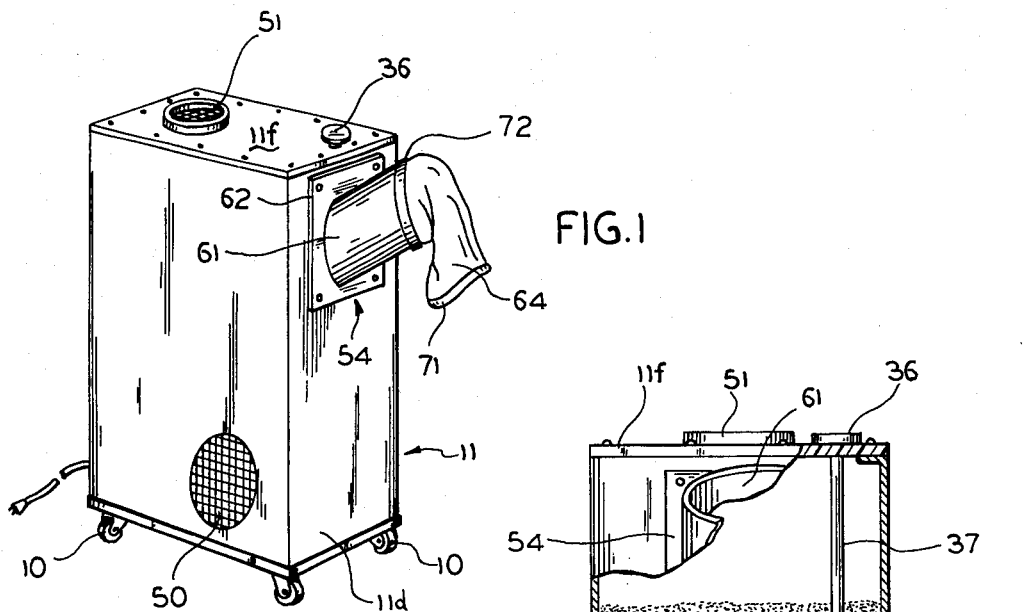
FIG. 1
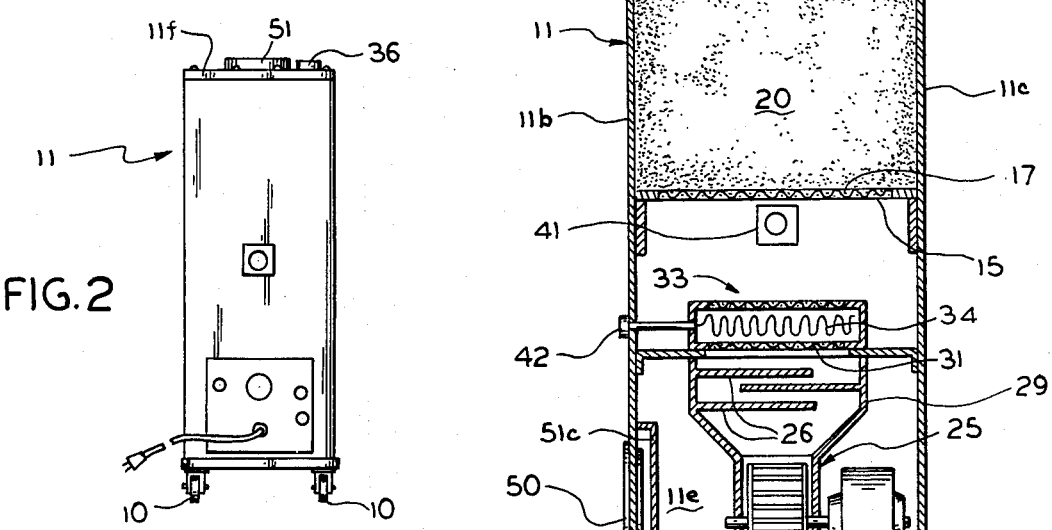
FIG. 2
FIG. 3
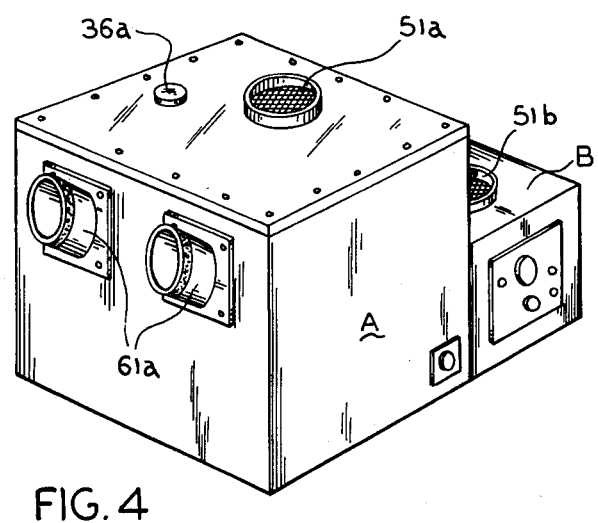
FIG. 4
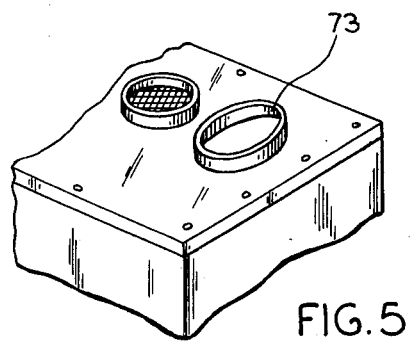
FIG. 5

APPARATUS FOR BODY MASSAGE USING A FLUIDIZED BED APPARATUS

RELATED PRIOR ART

This application relates to improvements in the apparatus and method disclosed in U.S. Pat. No. 3,860,800 issued Sept. 25, 1973.

BACKGROUND OF THE INVENTION

As used in this application the term "Fluidotherapy Unit" means apparatus for applying massage and heat or cold to the arms, legs and other parts of the body, whether human or animals, using a fluidized solids bed as the heat transfer medium. The apparatus is arranged to position the member being treated in intimate heat-conducting relation with a mass of finely divided solid particles by immersing the member in the mass. Meanwhile, the mass is rendered turbulent by forcing a gas, e.g. air, therethrough whereby the member is subjected to massaging action. The massaging action may or may not be accompanied by heat or cold imparted to the mass, e.g. by utilizing electrical heating elements or a refrigerant to heat or cool the body member, as the case may be.

The reference patent discloses an early form of apparatus for providing massage by subjecting a body member to the massaging action of an ebullient, heated bed of particles.

SUMMARY OF THE INVENTION

The present invention is directed to a more versatile apparatus so constructed and arranged as to lend itself to use by an operator having limited skills by the provision of simple, safe, foolproof components and comfortable accommodation of the patient.

In another aspect the invention is carried into practice in modular form, for example, by providing basic units primarily designed for one leg which may be quickly converted and/or assembled with other units to accommodate two legs and, similarly, for other body members. Additional openings may be provided to permit the therapist to manipulate the body member during therapy. In the case where several members are to be treated concurrently by the same regimen the modules may share some components in common.

In still another aspect the cabinet may be provided with side openings for locating a limb within the cabinet. This capacity of the apparatus is of considerable importance since a freely suspended limb may become edematous.

DESCRIPTION OF THE DRAWING

FIG. 1 is a perspective view of a basic unit capable of receiving a leg or an arm;

FIG. 2 is a front elevational view of the control side of a unit as shown in FIG. 1;

FIG. 3 is a vertical cross section to show the interior construction of a typical unit;

FIG. 4 is a perspective view of a combined unit to receive two arms, two hands, or an elbow or foot through the top;

FIG. 5 is a partial, perspective view of a unit to receive an elbow or foot;

DESCRIPTION OF CERTAIN PREFERRED EMBODIMENTS

Figure 6:
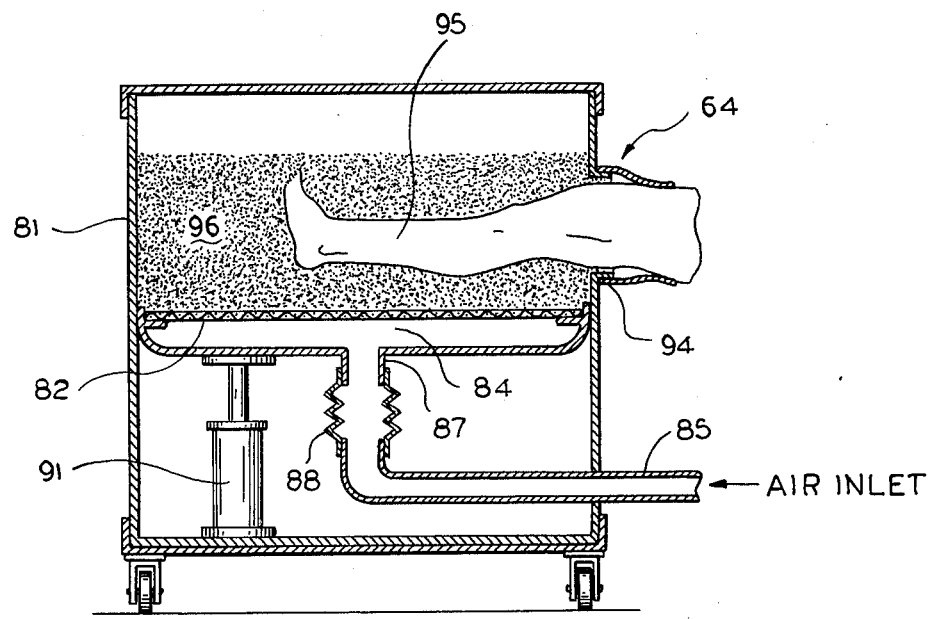
FIG. 6 is a more-or less diagrammatic showing of a unit which includes means for vertical adjustment.

Reverting to the drawing, there is shown (FIGS. 1, 2 and 3) a cabinet 11 of sheet steel or a laminated composite comprising a bottom wall 11a, side walls 11b, 11c, end walls 11d, 11e and a top wall 11f, this latter being of transparent plastics composition to permit viewing of the inside of the cabinet as well as the member undergoing treatment. Casters 10 are desirably secured to the bottom of the cabinet 11.

A horizontal, perforate plate 15 is supported within the cabinet 11 to provide for upward circulation of heated air, and a transverse sheet of porous material 17 is carried thereabove. The mesh and thickness of the plate 15 and sheet 17 is such as to support the mass 20 of particulate material, comprising the bed, e.g. a powdered solid, and, at the same time, allow passage of air under pressure therethrough from a motor-driven blower 25. If necessary, the output from the blower 25 is decreased in velocity, by an electronic motor controller. The noise of the motor is muffled by baffles 26 set into a casing 29 and then through a screen 31 where it meets an electric heater 33, e.g. a Calrod element 34, depicted diagrammatically in the drawing. The air is thus filtered and heated. A manually-controlled regulator 41 is employed to regulate and maintain the output of the heater 34 at a level appropriate to the treatment prescribed. The heated air then passes into the bed 20 via the distribution plate 15 and screen 17, which latter is designed to yield the pressure drop required for proper fluidization.

A thermometer 36 has its bulb 37 immersed in the bed 20 and is desirably of the dial type for convenience of reading. Thermistor sensors with digital readouts may also be used. Preferably, a high-temperature cut-off is connected in circuit with the blower motor to shut off the heater in the event of failure of the motor. Means 41 are also provided to control the circuit to the heater 34 in the event of malfunction permitting delivery of air too hot or too cold to be tolerated by the patient.

A grille 50, together with noise muffling means 51c, serves as an entrance port for air being drawn into the cabinet by the blower 25. An exhaust port 51 equipped with a filter screen serves as an exit for spent air from the casing. In the case of a "cold unit", the air is recirculated to the inlet port 50 to conserve refrigeration. It will be apparent that the apertures in the port will be smaller than the average size of the particles comprising the bed.

The patient's body member undergoing treatment will be introduced through the opening 73 into the top of the cabinet or through a port 54 comprising a section of tubing 61 mounted on a flange 62 on the side of the cabinet. A fabric sleeve 64 is secured on the free end of the tubing section 61. The other end of the sleeve 64 has an elastic garter or a Velcro closure of a size to encircle the patient's body member to preclude escape of particles.

The positioning of the tubing 61 enables the patient's limb to be treated horizontally. A Velcro fastener or elastic band 72 at the inner end of the sleeve 64 and a like band 71 at the outer end seal against escape of particles.

It has been found that attachment and detachment of the sleeve 64 from the unit may be accomplished more rapidly by the use of the fastening elements known under the trademark Velcro. Such means are well known and require no elaboration.

FIG. 4 illustrates a modified form of apparatus capable of treating two arms or two legs simultaneously. An elbow or foot may also be treated through the top opening 73 (FIG. 5) or a suitably-controlled opening in the side. Opening 73 must, of course, be fitted with a sleeve, such as 64. The construction and function are believed to be clear by reference to the preceding description. The two cabinets, A and B respectively, house components fully described in connection with FIGS. 1 to 3 but not duplicated in this modification. One unit A contains the fluidized solids bed and another unit B encloses the blower, blower motor and controls. Versatility is enhanced by such modular arrangements which may be connected at will by the use of sections of flexible tubing and flexible electrical conductors and connectors as described. For example, an assembly of suitable modules may serve an arm of one patient and a leg of another patient concurrently.

By closing off the heater 34 air at room temperature may be employed to agitate the bed 20. This procedure will allow massage without heat. Alternatively, means, whether integrated or a separate source, may circulate refrigerated air through the bed for use in cases where circulation of cold air about the body member is to be combined with the advantages of the agitated bed.

The invention apparatus lends itself to various modifications affording great versatility. For example, one arrangement involves seating the patient on a bicycle saddle mounted on a stable frame, with the foot or feet being treated suspended freely in the fluidized bed. For this purpose an adjunct or adjuncts such as 64 is mounted on the top wall 11f (FIG. 1). In the case where hot water is employed to benefit the patient, a tank (not shown) is substituted for the fluidized bed. Obviously, any well-known means may be used to adjust and regulate the water temperature as directed by the physician. If desired the aforementioned saddle may be carried on the piston of a hydraulic jack in order to position the patient comfortably with respect to the apparatus.

It is within contemplation to provide arm and back rests for further comfort.

One encouraging feature of the invention reside in its use for treating cancer. The M. D. Anderson Hospital in Houston, Texas, has been subjecting the human body and its members to heat and heat in conjunction with chemotherapy, the heat being applied through the medium of a fluidized solids bed. When drugs are used it has been found that the therapeutic action of the drug is accelerated.

Rather than employ finely-divided mineral material as the particles of the bed, I prefer to use a comminuted cellulose derivative, e.g., corn cobs. In accordance with generally accepted practice, the term "mesh" refers to U.S. Sieve Series, ASTM-E-11-61(Standard Seive Designation). Not only is this alternative compatible with the patient's skin but is incapable of causing accumulation of an electrostatic charge which, under some conditions, may be troublesome. A preferred product bears the trademark MAIZO and is available from Michael Wood Products Co., Garfield, N.J. Applicant prefers a 50—50 blend of 10 mesh and 20 mesh. However, for some applications particles as small as 50 to 100 mesh may be preferred.

FIG. 6 is a more-or-less diagrammatic side elevation of a modified form of apparatus having means for adjustment to accommodate variation in the vertical height of a limb, e.g. a leg. In this case an enclosure 81 is defined by side walls and has the perforate support plate 82 below which is the plenum chamber 84. Air under pressure, either hot or cold, is admitted through a pipe 85 forming an entrance to the chamber 84. A vertical section 87 comprises a convoluted flexible bellows 88 to accommodate the change in length of the section 87 in accordance with vertical adjustment. A jack, e.g. a hydraulic jack, 91, is positioned between a fixed support and the bottom of the plenum chamber to raise and lower the same in order to achieve the desired height of the fluidized bed in relation to the patient's limb. It will be understood that the opening 94 is of a size to permit comfortable reception of the limb, e.g. the leg, 95. As referred to hereinabove a garter, Velcro ring or other convenient means will be arranged to seal the opening 94 with respect to the limb to preclude egress of the fluidized medium 96.

It will also be understood that suitable gaskets will be provided where necessary to seal the enclosure 81 against escape of the fluidized particles.

Figure 7:
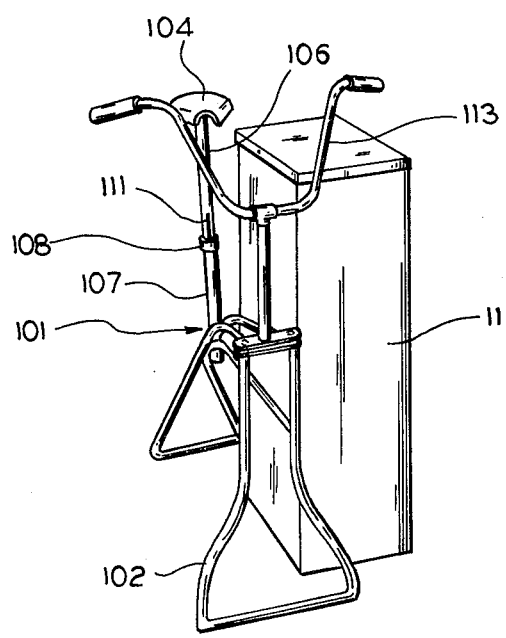
FIG. 7 is a side view showing a saddle-type support for the patient.

In certain cases where the patient is to undergo massage with a leg down in the bed, whether extended or bent at the knee, he is obliged to assume a position which is far from comfortable and therefore tiring. In this event a novel seat is provided as shown in FIG. 7.

A frame 101 is provided with legs 102, the frame being desirably anchored to the cabinet 11 but may be free-standing. A saddle seat 104 which may be a conventional bicycle seat is carried at the upper end of a post 106 adjustably received in a tubular member 107. A threaded clamping ring 108 cooperates with the slots 111 to enable vertical adjustment of the seat 104 in a well-known manner to locate the patient in a comfortable position while massage proceeds. If desired the patient's hands may rest on handlebars 113 to supplement the support lent by the seat 104.

I claim:

1. Apparatus for therapeutic massage of parts of the human body comprising a cabinet, a chamber in said cabinet, said chamber having a porous bottom wall and side walls together defining a space, a mass of solid particles contained in said space to constitute a bed in which the body part may be immersed, means to force gas upwardly through the porous wall and bed to create and maintain an ebullient condition of the particles, a tubular member through which the body part may be passed into the chamber for immersion in the bed, said member extending from one of said side walls, the axis of the tubular member being at an angle upwardly from the horizontal, the highest point of the interior of the tubular member being above the highest level of the mass when in a turbulent state to preclude escape of the particulate matter outwardly through the member.

2. Apparatus in accordance with claim 1 further characterized by means to heat the mass of particles.

3. Apparatus in accordance with claim 2 further characterized by a compartment below said chamber, said bottom wall is provided with a plurality of openings for passage of gas from the compartment through the bed, a source of gas under pressure and duct means providing communication between the openings and compartment.

4. Apparatus in accordance with claim 1 in which the free end of the tubular member carries a flexible sleeve, said free end having a peripheral constrictive garter to embrace the body member and to seal the interior of the chamber against escape of particles therefrom.

5. Apparatus for therapeutic massage of the human body in accordance with claim 1, wherein the particulate matter comprises a cellulose derivative.

6. Apparatus in accordance with claim 5 in which the particles are of about 10 to 50 mesh average size.

7. Apparatus in accordance with claim 1 further characterized in that the gas-forcing means is motor-driven blower, a duct forms the exhaust side of the blower and the heating means are positioned in the duct.

8. The method of massaging a part of the human body comprising the steps of:
(a) providing a closed chamber containing a mass of finely-divided cellulose derivative
(b) locating the body part in the mass while supporting the same with the part immersed to the predetermined degree;
(c) sealing the spaces between the chamber walls and body part
(d) heating the mass to a predetermined temperature while
(e) forcing a gas therethrough to produce turbulent action of the mass;
(f) allowing the body part to remain so immersed for a predetermined time;
(g) removing the body part from the mass.

9. The method of massaging a part of the human body comprising the steps of:
(a) providing a closed chamber containing a mass of finely-divided corn cobs;
(b) locating the body part in the mass while supporting the same with the part immersed to the predetermined degree;
(c) sealing the spaces between the chamber walls and body part
(d) refrigerating the mass to a predetermined temperature while
(e) forcing a gas therethrough to produce turbulent action of the mass;
(f) allowing the body part to remain so immersed for a predetermined time;
(g) removing the body part from the mass.

10. The method of providing localized massage of a part of the human body by immersing the part of a bed of fluidized solid particles comprising the steps of:
(a) providing a chamber to contain a mass of the particles;
(b) placing the body part on a support with the part to be treated substantially immersed in the mass;
(c) sealing the body part with respect to the ambient air;
(d) forcing a gas through the mass to induce turbulence thereof for a predetermined time; and
(e) removing the part from the mass.

11. The method in accordance with claim 10 further including the further step of heating said mass for a predetermined part of the period of turbulence.

12. The method in accordance with claim 11 further including the further step of refrigerating the said mass for a predetermined part of the period of turbulence.

13. Apparatus for massage of a part of the human body comprising a cabinet, a support plate forming a compartment in the cabinet and having adjustable vertical movement therewithin, said compartment containing a bed of solid particles in which the body part is immersed to a predetermined depth, the particles, when agitated, providing a fluidized bed to subject the body part to massaging action, means to support the compartment for vertical adjustment, means to vertically adjust the compartment a plenum chamber below the compartment, a plurality of passages providing communication between the compartment and plenum chamber and means to feed a gas under pressure into the plenum chamber and through the bed to agitate said particles, and duct means to deliver a hot or cold gas to the plenum chamber.

14. Apparatus for massage of a part of the human body comprising a cabinet, means defining a chamber within the cabinet, said chamber receiving a bed of solid particles in which the body member is immersed to the predetermined degree, means to fluidize the bed, means to adjust the vertical position of the chamber to alter the said degree of immersion and means to support the body member with respect to the chamber for adjusting movement jointly with the bed.

15. In combination with apparatus for subjecting a person's leg to the massaging action of a fluidized solids bed, the apparatus including a framework, a compartment to receive the bed and means to support the leg relative to the bed during treatment, a saddle seat carried on the framework upon which the patient's posterior may rest.

16. The combination in accordance with claim 15 further characterized by means to adjust the seat relative to the bed.

* * * * *